(12) United States Patent
Loeb et al.

(10) Patent No.: US 6,735,474 B1
(45) Date of Patent: May 11, 2004

(54) IMPLANTABLE STIMULATOR SYSTEM AND METHOD FOR TREATMENT OF INCONTINENCE AND PAIN

(75) Inventors: Gerald E. Loeb, So. Pasadena, CA (US); Francis J. R. Richmond, So. Pasadena, CA (US); Carla M. Mann, Los Angeles, CA (US); Michael A. Faltys, Northridge, CA (US); Todd K. Whitehurst, Sherman Oaks, CA (US); James P. McGivern, Stevenson Ranch, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 339 days.

(21) Appl. No.: 09/642,979

(22) Filed: Aug. 18, 2000

Related U.S. Application Data

(63) Continuation-in-part of application No. PCT/US99/14775, filed on Jun. 29, 1999.
(60) Provisional application No. 60/173,054, filed on Dec. 24, 1999, and provisional application No. 60/091,762, filed on Jul. 6, 1998.

(51) Int. Cl.$^7$ ............................................. A61N 1/36
(52) U.S. Cl. .......................................................... 607/41
(58) Field of Search ............................. 607/41, 39, 40, 607/45, 46, 72, 61

(56) References Cited

U.S. PATENT DOCUMENTS

| | | |
|---|---|---|
| 3,646,940 A | 3/1972 | Timm et al. |
| 3,650,276 A | 3/1972 | Burghele et al. |
| 3,667,477 A | 6/1972 | Susset et al. ............... 128/419 |

(List continued on next page.)

FOREIGN PATENT DOCUMENTS

| | | |
|---|---|---|
| EP | 245547 B1 | 8/1990 |
| WO | 9718857 | 5/1997 |
| WO | 9837926 | 9/1998 |

(List continued on next page.)

OTHER PUBLICATIONS

Walter, et al., "Short–Term Bladder Wall Response to Implantation of Microstimulators", The Journal of Spinal Cord Medicine, vol. 20, No. 3, (Apr. 11, 1997), pp. 319–323.
UroSurge—SANS 2; printed Mar. 2, 2000; pp 1–2.
UroSurge—SANS (Stoller Afferent Nerve Stimulation) Device; printed Mar. 2, 2000; pp 1–5.

(List continued on next page.)

*Primary Examiner*—Kennedy Schaetzle
(74) *Attorney, Agent, or Firm*—Laura Haburay Bishop; Bryant R. Gold

(57) ABSTRACT

A method and system for treatment of incontinence and/or pelvic pain includes the injection or laparoscopic implantation of one or more battery- or radio frequency-powered microstimulators (10) beneath the skin of the perineum and/or adjacent the tibial nerve. The devices are programmed using radio-frequency control via an external controller (20, 30)) that can be used by a physician to produce patterns of output stimulation pulses judged to be efficacious by appropriate clinical testing to diminish symptoms. The stimulation program is retained in the microstimulator device (10) or external controller (20) and is transmitted when commanded to start and stop by a signal from the patient or caregiver. The system and method reduce the incidence of unintentional episodes of bladder emptying by stimulating nerve pathways (8) that diminish involuntary bladder contractions, improve closure of the bladder outlet, and/or improve the long-term health of the urinary system by increasing bladder capacity and period between emptying. The incidence of fecal incontinence is similarly reduced or eliminated. Furthermore, the system and method reduce or eliminate the incidence of pelvic pain by chronically stimulating nerve pathways that derive from the sacral roots using a miniature implantable neurostimulator that can be implanted with a minimal surgical procedure. Moreover, the system and method allow a patient to be taught to receive one or more patterns of neural stimulation that can be prescribed by a physician and administered without continuous oversight by a clinical practitioner.

23 Claims, 4 Drawing Sheets

U.S. PATENT DOCUMENTS

| | | | |
|---|---|---|---|
| 3,870,051 | A | 3/1975 | Brindley |
| 4,387,719 | A | 6/1983 | Plevnik et al. |
| 4,406,288 | A | 9/1983 | Horwinski et al. |
| 4,431,001 | A | 2/1984 | Hakansson et al. |
| 4,569,351 | A | 2/1986 | Tang |
| 4,585,005 | A | 4/1986 | Lue et al. |
| 4,607,639 | A | 8/1986 | Tanagho et al. |
| 4,703,755 | A | 11/1987 | Tanagho et al. |
| 4,739,764 | A | 4/1988 | Lue et al. .................... 128/419 |
| 4,771,779 | A | 9/1988 | Tanagho et al. ............ 128/419 |
| 5,094,242 | A | 3/1992 | Gleason et al. ............. 128/642 |
| 5,193,539 | A | 3/1993 | Schulman et al. .......... 128/419 |
| 5,193,540 | A | 3/1993 | Schulman et al. .......... 128/419 |
| 5,199,430 | A | 4/1993 | Fang et al. |
| 5,312,439 | A | 5/1994 | Loeb .............................. 607/2 |
| 5,324,316 | A | 6/1994 | Schulman et al. ............ 607/61 |
| 5,358,514 | A | 10/1994 | Schulman et al. |
| 5,405,367 | A | 4/1995 | Schulman et al. ............ 607/61 |
| 5,562,717 | A | 10/1996 | Tippey et al. ................. 607/41 |
| 5,571,148 | A | 11/1996 | Loeb et al. |
| 5,702,428 | A | 12/1997 | Tippey et al. ................. 607/41 |
| 5,957,965 | A | 9/1999 | Moumane et al. .......... 607/117 |
| 5,984,854 | A | 11/1999 | Ishikawa et al. ............... 600/9 |
| 6,026,326 | A | 2/2000 | Brady |
| 6,051,017 | A | 4/2000 | Loeb et al. |
| 6,061,596 | A | 5/2000 | Richmond et al. ............ 607/41 |
| 6,104,955 | A | 8/2000 | Bourgeois ..................... 607/40 |
| 6,104,960 | A | 8/2000 | Duysens et al. |
| 6,185,452 | B1 * | 2/2001 | Schulman et al. ............ 604/20 |
| 6,208,894 | B1 | 3/2001 | Schulman et al. |
| 6,240,316 | B1 | 5/2001 | Richmond et al. |
| 6,360,750 | B1 | 3/2002 | Gerber et al. |
| 6,407,308 | B1 * | 6/2002 | Roe et al. .................... 604/361 |
| 2001/0002441 | A1 | 5/2001 | Boveja |

FOREIGN PATENT DOCUMENTS

| | | |
|---|---|---|
| WO | 9843700 | 10/1998 |
| WO | 9843701 | 10/1998 |
| WO | WO-00/01320 A3 | 1/2000 |
| WO | WO-00/19939 A1 | 4/2000 |
| WO | WO-00/25859 A1 | 5/2000 |
| WO | WO-01/52729 A2 | 7/2001 |
| WO | WO-01/54767 A1 | 8/2001 |
| WO | WO-01/60445 A2 | 8/2001 |
| WO | WO-02/20086 A1 | 3/2002 |

OTHER PUBLICATIONS

UroSurge—SANS AUA Abstract; printed Mar. 2, 2000; pp 1–2.

IC in the News! ICN Feature Stories; printed Mar. 2, 2000; pp 1–7.

What is Medtronic InterStim Therapy for Urinary Control; printed Mar. 2, 2000; pp 1–2.

Medtronic's InterStim Therapy for Urinary Co . . . : For People with Bladder Control Problem; printed Mar. 2, 2000; pp 1–2.

Medtronic's InterStim Therapy for Urinary Control: For Health Care Professionals; printed Mar. 2, 2000; pp 1–2.

Medtronic InterStim Urinary Control—FAQ's; printed Mar. 2, 2000; pp 1–7.

Our Products: Incontinence Therapies: Innova® PFS; printed Mar. 2, 2000; pp 1–2.

Our Products: Incontinence Therapies; printed Mar. 2, 2000; pp 1–2.

Lower Back Pain, Neck Pain, Arthritis—Pain Management & Muscle Stimulation—Ottawa . . . ; printed Mar. 2, 2000; p 1.

McGuire EJ, et al.; Treatment of Motor and Sensory Detrusor Instability by Electrical Stimulation; Journal of Urology; 1983; 129 (1):78–79.

Murray KH; Letter Re: Treatment of Motor and Sensory Detrusor Instability by Electrical Stimulation and Re: The Neurophysiological Basis of Bladder Inyhibition in Response to Intravaginal Electrical Stimulation; Journal of Urology; 1984; 131 (2):356.

Crocker M, et al.; Transcutaneous Electrical Nerve Stimulation in Urinary Retention; Southern Medical Journal, 1985; 78 (12):1515–1516.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

Shealy, et al., "Electrical Inhibition of Pain by Stimulation of the Dorsal Column", Anesthesia and Analgesia, vol. 46, (1967), pp. 489–491.

Vodusek, et al., "Detrusor Inhibition Induced by Stimulation of Pudendal Nerve Afferents", Neurourology and Urodynamics, vol. 5, (1986), pp. 381–389.

Vodusek,et al., "Detrusor Inhibition on Selective Pudendal Nerve Stimulation in the Perineum", Neurourology and Urodynamics, vol. 6, (1988), pp. 389–393.

Sundin, et al., "Detrusor Inhibition Induced from Mechanical Stimulation of the Anal Region and From Electrical Stimulation of Pudendal Nerve Afferents", Investigative Urology, vol. 11, No. 5, (1974), pp. 374–378.

Ohlsson, et al., "Effects of External and Direct Pudendal Nerve Maximal Electrical Stimulation in the Treatment of the Uninhibited Overactive Bladder", British Journal of Urology, vol. 64, (1989), pp. 374–380.

Fall, et al., "Electrical Stimulation. A Physilogic Approach to the Treatment of Urinary Incontinence", Urol Clin North Am, vol. 18, No. 2 (May 1991), pp. 393–407.

Malouf, et al., "Permanent Sacral Nerve Stimulation for Fecal Incontinence", Ann Surg, vol. 232, No. 1, (Jul. 2000), pp. 143–148.

Schmidt, et al., "Sacral Nerve Stimulation for Treatment of Refractory Urinary Urge Incontinence. Sacral Nerve Stimulation Study Group", J Urol, vol. 162, No. 2, (Aug. 1999), pp. 352–357.

Shaker, et al., "Sacral Nerve Root Neuromodulation: an Effective Treatment for Refractory Urge Incontinence", J Urol, vol. 159, No. 5, (May 1998), pp. 1516–1519.

Shafik, et al., "Sacral Root Stimulation for Controlled Defecation", Eur Surg Res, vol. 27, No. 1, (1995), pp. 63–68.

Teague, et al., "Electric Pelvic Floor Stimulation. Mechanism of Action." Invest Urol, vol. 15, No. 1 (Jul. 1977), pp. 65–69.

Merrill, "The Treatment of Detrusor Incontinence by Electrical Stimulation", J Urol, vol. 122, No. 4, (Oct. 1979), pp. 515–517.

Merrill, et al., "Urinary Incontinence. Treatment with Electrical Stimulation of the Pelvic Floor", Urology, vol. 5, No. 1, (Jan. 1975), pp. 67–72.

Sawan, et al., "Computerized Transcutaneous Control of a Multichannel Implantable Urinary Prosthesis", IEEE Transactions on Biomedical Engineering, vol. 39, No. 6, (Jun. 1, 1992), pp. 600–609.

* cited by examiner

IMPLANTABLE STIMULATOR SYSTEM AND METHOD FOR TREATMENT OF INCONTINENCE AND PAIN

This application is a continuation-in-part (CIP) of copending PCT patent application Serial Number PCT/US99/14775 filed Jun. 29, 1999, which in turn claims priority to, and the benefit of, prior U.S. provisional patent application Serial No. 60/091,762, filed Jul. 6, 1998. This application also claims the benefit of copending U.S. provisional patent application Serial No. 60/173,054, filed Dec. 24, 1999. These three applications are incorporated herein by reference.

FIELD OF THE INVENTION

The present invention relates to implantable stimulator systems, and more particularly to an implantable stimulator system utilizing one or more implantable microstimulators for treating incontinence and/or pain.

BACKGROUND OF THE INVENTION

Urinary Incontinence is a clinical condition characterized by failure to hold urine in the bladder under normal conditions of pressure and filling. The most common forms of the disorder can arise from either a failure of muscles around the bladder neck and urethra to maintain closure of the urinary outlet (so-called stress incontinence) or from abnormally heightened commands from the spinal cord to the bladder that produce unanticipated bladder contractions (so-called urge incontinence). Many patients exhibit a grouping of symptoms suggesting that these disorders may occur simultaneously in the same individual (so-called mixed incontinence).

It is well known in the art that electrical stimulation in the region of the pelvic floor can decrease the severity of incontinence. The improvement is believed to be attained through at least three mechanisms: (1) by changing the reflex thresholds of the bladder muscles responsible for bladder emptying, (2) by strengthening the muscles that maintain closure on the bladder outlet, and (3) by changing the state of the neural pathways, musculature and/or bladder during and beyond the period of stimulus application.

The therapies currently available for incontinence have generally been directed at improving muscle condition, as disclosed, e.g., in applicant's prior document WO97/18857 (PCT/US96/18680), published May 29, 1997. Bladder hyper-reflexia and detrusor instability have proven more difficult to treat. However, evidence in the art suggests that it can be improved in many individuals by stimulating peripheral nerves or nerve roots continuously or intermittently to modulate transmission of excitatory nerve signals to the bladder muscles.

Several external and implantable approaches have been used to stimulate the nerves supplying the bladder and pelvic region in order to decrease the episodic incidences of unintentional bladder emptying. Those who strengthen periurethral muscles have usually employed vaginal or anal electrode assemblages to stimulate muscle contractions repeatedly. These methods are limited in their portability and are often poorly accepted by patients because they are inconvenient and often associated with unpleasant skin sensations. Further, the methods are inadequate for the treatment of urge incontinence in which continual electrical stimulation is commonly needed to diminish or inhibit the heightened reflexes of bladder muscles.

For the treatment of urge incontinence, surgically implanted stimulators under battery or radio-frequency control have been described in the art. These stimulators have different forms, but are usually comprised of an implantable control module to which is connected a series of leads that must be routed to nerve bundles in either the sacral roots emanating from the spinal cord, or the nerves supplying muscles, skin or other structures in the pelvic region. The implantable devices are relatively large, expensive and challenging to implant surgically. Thus, their use has generally been confined to patients with severe symptoms and the capacity to finance the surgery.

These same types of therapies have been used to treat pelvic pain, with the same drawbacks. For instance, neurostimulation of the sacral nerve roots has been demonstrated to relieve pelvic pain in patients with intractable chronic pelvic pain. Other devices used for both incontinence and pelvic pain require that a needle electrode(s) be inserted through the skin during stimulation sessions. These devices may only be used acutely, and may cause significant discomfort.

More recently, small, implantable microstimulators have been introduced that can be injected into soft tissues through a cannula or needle. See, e.g., U.S. Pat. Nos. 5,324,316 and 5,405,367, both of which patents are incorporated herein by reference. What is needed is a way to effectively use such small, implantable microstimulators for the purpose of treating incontinence and/or pelvic pain.

SUMMARY OF THE INVENTION

The system and method taught in this invention include the injection, direct implantation, endoscopic, or laparoscopic implantation of one or more battery- or radio-frequency-powered microstimulators beneath the skin of the perineum. The system and method taught also include the injection, direct implantation, endoscopic, or laparoscopic implantation of one or more battery- or radio-frequency-powered microstimulators on or near the tibial nerve. The devices are programmed using radio-frequency control via an external controller that can be used by a physician to produce patterns of output stimulation pulses judged to be efficacious by appropriate clinical testing. Such stimulation program is retained in the device or external controller and is transmitted when commanded to start and stop by a signal from the patient or caregiver.

It is an object of this invention to reduce or eliminate the incidence of unintentional episodes of bladder emptying (i.e. incontinence) as well as other dysfunctions of perineal structures, such as urgency and frequency by stimulating nerve pathways that diminish involuntary bladder contractions, improve closure of the bladder outlet, and/or improve the long-term health of the urinary system by increasing bladder capacity and thus, the time period between emptying. As one example of another dysfunction of perineal structures, it is also an object of this invention to similarly reduce or eliminate the incidence of fecal incontinence.

Another object of this invention is to reduce or eliminate pelvic pain by chronically stimulating nerve pathways that derive from the sacral roots using an implantable neurostimulator that is implanted with a minimal surgical procedure.

It is a further object of this invention to teach a method whereby a patient can receive one or more patterns of neural stimulation that can be prescribed by a physician and administered without continuous oversight by a clinical practitioner.

It is a feature of the invention to meet the above-identified objects of the invention using a system of small, implantable microstimulators of the type described in, or similar to those described in, the above-referenced patents and/or patent applications.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
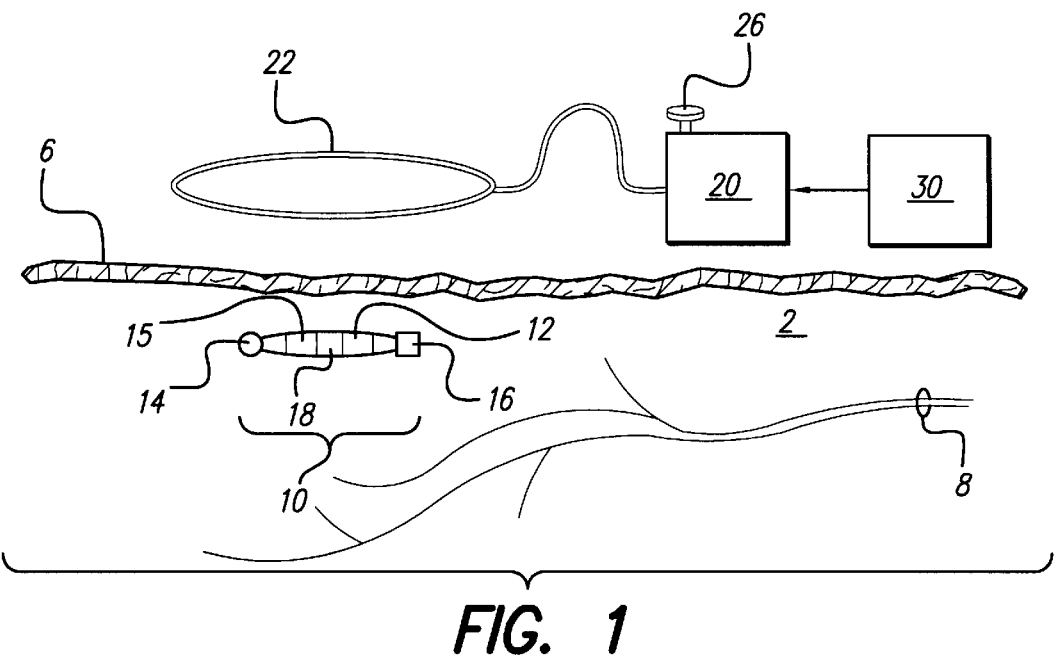
FIG. 1 illustrates a programming system for use with an implantable microstimulator.

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention utilizes one or more implantable microstimulators. The microstimulators of the present invention are preferably of the type referred to as BION™ devices. The following documents describe various features and details associated with the manufacture, operation and use of BION microstimulators, and are all incorporated herein by reference:

| Application/ Patent/ Publication No. | Filing/ Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| PCT Publication WO 98/37926 | published Sep. 3, 1998 | Battery-Powered Patient Implantable Device |
| PCT Publication WO 98/43700 | published Oct. 8, 1998 | System of Implantable Devices For Monitoring and/or Affecting Body Parameters |
| PCT Publication WO 98/43701 | published Oct. 8, 1998 | System of Implantable Devices For Monitoring and/or Affecting Body Parameters |
| U.S. patent application 09/077,662 | filed May 29, 1998 | Improved Implantable Microstimulator and Systems Employing Same |
| | published September 1997 | Micromodular Implants to Provide Electrical Stimulation of Paralyzed Muscles and Limbs, by Cameron, et al., IEEE Transactions on Biomedical Engineering, Vol. 44, No. 9, pages 781–790. |

The microstimulator is preferably implanted with a surgical insertion tool such as described in U.S. Provisional Patent Application No. 60/184,561, or is injected (e.g., via a hypodermic needle). Alternatively, the device may be implanted via conventional, endoscopic, or laparoscopic surgical techniques. A more complicated surgical procedure may be required for fixing the neurostimulator in place.

In one preferred embodiment the microstimulator comprises two, leadless electrodes. However, either or both electrodes may alternatively be located at the ends of short, flexible leads as described in U.S. Provisional Patent Application No. 60/156,980, filed Oct. 1, 1999, which is incorporated herein by reference. The use of such leads may permit electrical stimulation to be directed more locally a short distance from the surgical fixation of the bulk of the implantable stimulator. In a preferred embodiment, the leads are no longer than about 100 to 120 mm.

Advantageously, the small size of the microstimulators referenced above permits insertion of these devices beneath the skin of the perineum, for instance, where they have the capability to stimulate the nerves and muscles in regions surrounding the urethra and anus.

For purposes of this patent application, it is sufficient to note that radio-frequency controlled microstimulators receive power and control signals from an extra corporeal antenna coil via inductive coupling of a modulated radio-frequency field. Battery-operated microstimulators incorporate a power source within the device itself but rely on radio-frequency control to program stimulus sequences and to recharge the power source, when needed. In accordance with the present invention, each implanted microstimulator may be commanded to produce an electrical pulse of a prescribed magnitude and duration and at a repetition rate sufficient to cause stimulation of nerve axons.

The ability to implant small, less expensive microstimulators by injection or laparoscopic insertion, rather than major surgery, significantly reduces the expense and complication rates of implantable technologies for urinary and/or fecal incontinence. For some patients, use of the stimulator for only a few hours per day or week will improve the symptomatology of incontinence and/or pelvic pain. In such patients, RF controlled devices provide an adequate amount of stimulation if used intermittently for only a few hours per day to greatly decrease the incidence of incontinent and/or painful episodes. For many other patients, however, a continuous or intermittent stimulation throughout the day is needed. These patients may best utilize a stimulator that has a self-contained power source sufficient to deliver repeated pulses for several hours and that can be recharged repeatedly. In accordance with the teachings of the present invention, the use of a microstimulator with a rechargeable battery thus provides these patients the portability needed to free the patient from reliance on radio-frequency power delivery.

A battery-powered microstimulator suitable for use with the present invention, and a control system for use with such battery-powered microstimulator, is fully described in earlier referenced WO98/37926, published Sep. 3, 1998; WO98/43700, published Oct. 8, 1998; and WO98/43701, published Oct. 8, 1998.

Turning to FIG. 1, a preferred embodiment of the invention is illustrated. As seen In FIG. 1, a rechargeable, battery-powered microstimulator 10 is implanted into subcutaneous region 2, where current pulses delivered from its electrodes 14 and 16 stimulate nerve fibers 8. Nerve bundles in the subcutaneous region may carry somatic sensory axons supplying receptors in skin and muscle and somatic motor axons supplying skeletal muscle, as well as autonomic axons supplying visceral and glandular structures and smooth muscle.

When a sensory nerve is stimulated, it produces an electrical impulse that is transmitted along the axon into the dorsal horn of the spinal cord, where it can produce perceptible sensations, modulation of spinal cord circuits and reflex effects on motor pathways.

When a motor nerve is stimulated, electrical impulses are conveyed through its many peripheral branches that supply muscle fibers and elicit contractions in them.

Microstimulator 10 contains electronic circuitry 12 for receiving data and/or power from outside the body, preferably by inductive coupling. In a preferred embodiment, electronic circuitry 12 includes an inductive coil for receiving and transmitting radio frequency (RF) data and/or power, an integrated circuit (IC) chip for decoding and storing stimulation parameters and generating stimulation pulses (either intermittent or continuous), and additional discrete electronic components that may be required to complete the electronic circuit functions, e.g., a capacitor, resistor, coil, etc.

Electronic circuitry 12 dictates the amplitude and duration of the electrical current pulse, thereby determining the number of nerve fibers excited by each pulse. Advantageously, electronic circuitry 12 includes a programmable memory 18 for storing at least one set of stimulation and control parameters.

The preferred implantable stimulator 10 also includes a power source and/or power storage device 15. Possible power options, described in more detail below, include but are not limited to an external power source coupled to stimulator 10 via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is rechargeable, a means of recharging the power source (e.g., an RF link).

In a preferred embodiment, electronic circuitry 12 receives operating power and (if a rechargeable battery is included within the microstimulator) recharge power for the battery, and data to be stored in memory element 18 by inductive coupling from external controller 20 and its associated antenna coil 22. During an initial programming session after implantation of microstimulator 10, the prescribing physician uses a programming station 30 to download a pattern of stimulus pulse delivery to controller 20, which saves the information in nonvolatile memory. Each time the microstimulators 10 are recharged by controller 20, the stimulation parameters required from each microstimulator 10 are transmitted via coil 22, along with the power required for recharging. The stimulation parameters are stored in the memory element 18 of each microstimulator 10 as long as power storage device 15 has sufficient power to operate the microstimulator circuitry.

According to this preferred embodiment, program delivery is initiated by start and stop commands delivered by patient-governed control switch 26. In this and other preferred embodiments, controller 20 is a hand-held module containing a microprocessor and appropriate nonvolatile memory, such as electronically erasable programmable read-only-memory (EEPROM). In additional preferred embodiments, controller 20 operates to control implantable stimulator 10 by any of various means, including sensing the proximity of a permanent magnet located in controller 20, or sensing RF transmissions from the handheld controller 20. However, it will be evident to those of skill in electronic circuitry and computing that many different system architectures and components could be used to achieve similar functionality with either a battery-powered or radio frequency-powered microstimulator device.

A preferred stimulation location for purposes of the present invention is the pelvic floor. Direct stimulation of the pelvic floor nerves bypasses the potential recruitment of other unrelated nerve groups at the sacral roots. Nerves in this region that may be targeted for stimulation include the pudendal nerve, pelvic nerve, and the clitoral branches of the pudendal nerve.

The pudendal nerve and its branches are somatic nerves that originate from the sacral nerve roots S2, S3, and S4. These and other somatic nerves emanating from the sacral nerve roots are preferably stimulated to treat dysfunctions of perineal structures, such as urinary and/or bowel incontinence, urgency, frequency, and/or pain. For instance, stimulation of the urethral branch of the pudendal nerve may be used to inhibit defecation, thereby treating fecal incontinence. Additionally or alternatively, stimulation of the inferior rectal branch of the pudendal nerve, which innervates the external anal sphincter, may also inhibit defecation, thereby treating fecal incontinence. Stimulation of other somatic nerves innervating the rectum and/or colon may treat constipation, fecal retention, and/or colorectal hypomotility. Stimulation of one or more other pudendal nerve branches (e.g., the dorsal nerve of the clitoris/penis) may be used as a treatment of, e.g., urinary urge incontinence and/or detrusor hyperreflexia. Stimulation of nerves innervating the urethra and/or detrusor muscle may treat urinary retention, while stimulation of nerves innervating the internal and/or external urethral sphincter or their intramuscular branches may treat urinary stress incontinence. Stimulation of nerve (s) innervating the clitoris and/or vagina may treat vaginismus, dyspareunia, anorgasmia, or other female sexual dysfunction.

Stimulation parameters of, for instance, the pudendal nerve and other somatic nerves emanating from a sacral root will generally fall in the following ranges:

Frequency: 2–20 pulses per second (pps).

Duration: 50–350 microseconds (ps).

Amplitude: 1–5 volts at about 1–50 milliamps (mA).

It is to be understood that the above ranges are not absolute. Rather, they provide a guide for the stimulation parameters to be used. One of the attractive features provided by the invention is that the stimulation parameters can be adjusted, as required, until an appropriate and efficacious stimulation regime is achieved.

Another preferred stimulation location for purposes of the present invention is the tibial nerve. The tibial nerve is relatively easily accessible (i.e., relatively near the overlying skin with no muscle between the nerve and the skin) at two sited in the leg: at the level of the ankle, immediately posterior to the medial malleolus and posterior tibial artery and vein; and at the level of the knee, in the popliteal fossa (i.e., the back of the knee), immediately lateral to the popliteal artery and vein. Other sites along the tibial nerve, although not as easily accessible, are acceptable stimulator locations. A microstimulator may be planted unilaterally, or two or more microstimulators may be implanted bilaterally.

Once again, stimulation and control parameters may be adjusted to levels that are safe and efficacious and cause the least discomfort, and parameters may also be chosen to target specific neural populations and to exclude others. For example, relatively low frequency neurostimulation (i.e., less than about 50–100 Hz) may have an excitatory effect on surrounding neural tissue, whereas relatively high frequency neurostimulation (i.e., greater than about 50–100 Hz) may have an inhibitory effect.

For example, somatic nerves that originate from S2, S3, and S4 nerve roots, e.g. the pudendal nerve and its nerve branches, may be stimulated to treat incontinence, urgency, frequency, and/or pelvic pain. In one alternative, exciting the urethral branch of the pudendal nerve will inhibit defecation in some patients. Low-frequency electrical stimulation (e.g., less than about 50–100 Hz) is likely to produce such excitement. In another alternative, exciting other branches of the pudendal nerve, especially the dorsal nerve of the clitoris in the female and the dorsal nerve of the penis in the male, will prevent urination and/or defecation in some patients. Once again, low-frequency stimulation is likely to provide this excitement.

In another alternative, exciting the pudendal nerve at the point where it passes through the pudendal canal (a.k.a. Alcock's Canal) will prevent urination and/or defecation and/or will control pelvic pain in some patients. Once again, low-frequency stimulation is likely to provide this excitement.

As a further example, large diameter fibers (e.g., A-α and/or A-β fibers) respond to relatively lower current density stimulation compared with small diameter fibers (e.g., A-δ and/or C fibers). Typically, relatively large diameter nerve fibers respond to pressure and light touch, while smaller fibers respond to pain. For example, stimulation of the pudendal nerve with relatively low current density may cause a relatively non-painful (e.g., tingling) sensation that may treat incontinence in some patients.

The microstimulators of the type described in the referenced patents and patent publications represent a new class of generic implantable stimulators. These devices are microminiature, single-channel stimulators that can be injected/implanted through the use of a 12 gauge needle, the device of the above-referenced U.S. Provisional Patent Application No. 60/184,561, or similar device, in and around nerves and muscles. Under control of an RF coupled external transmitter, microstimulators provide precise patterns of muscle activation with a variety of programmable pulse durations and intensities. While each microstimulator is a single channel unit, the same external unit may control up to 256 stimulators that then work in harmonious combination to create a multichannel neuro-muscular control network. Because the microstimulators are injectable, they are minimally invasive, and may be injected in an outpatient environment posing little clinical risk, and reducing costs. If necessary, such microstimulators may be removed through a small surgical incision.

Advantageously, by implanting one or more microstimulators in the manner described herein so as to selectively stimulate appropriate nerves and/or tissue, it is possible to create a system which: (1) reduces or eliminates the incidence of unintentional episodes of bladder emptying by stimulating nerve pathways that diminish involuntary bladder contractions, (2) improves closure of the bladder outlet, (3) improves the long-term health of the urinary system by increasing bladder capacity and period between emptying and/or (4) reduces or eliminates pelvic pain.

According to one embodiment of the invention, a microstimulator operates independently. According to another embodiment of the invention, a microstimulator operates in a coordinated manner with other microstimulator(s), other implanted device(s), or other device(s) external to the patient's body. For instance, a microstimulator may control or operate under the control of another implanted microstimulator(s), other implanted device(s), or other device(s) external to the patient's body. A microstimulator may communicate with other implanted microstimulators, other implanted devices, and/or devices external to a patient's body via, e.g., an RF link, an ultrasonic link, or an optical link. Specifically, a microstimulator may communicate with an external remote control (e.g., patient and/or physician programmer) that is capable of sending commands and data to a microstimulator and that may be capable of receiving commands and data from a microstimulator.

Figure 2:
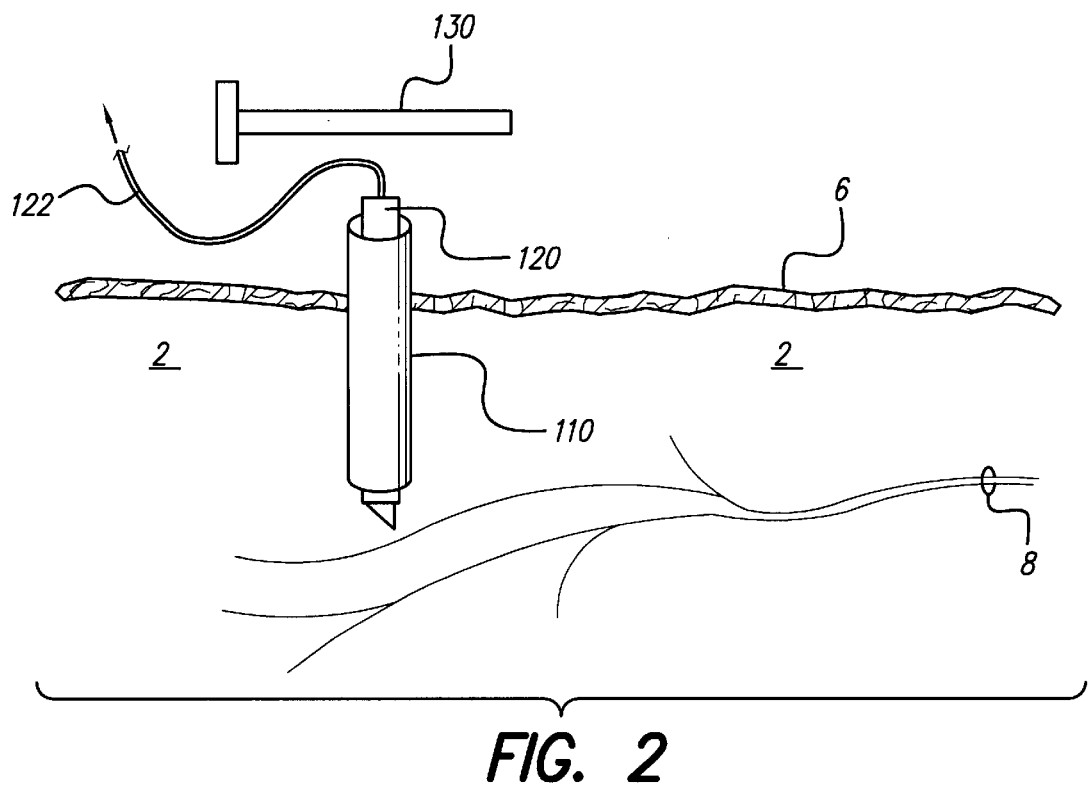
FIG. 2 shows an insertion system for use with an implantable microstimulator and an exemplary location for the microstimulator.

In accordance with one embodiment of the present invention, a microstimulator is injected into soft tissues by using an insertion device whose preferred embodiment is shown in FIG. 2. The hollow cannula 110 of the insertion device is comprised of a stiff, dielectric material with sufficient lubricity to permit the undamaged passage of device 10 therethrough. Probe 120 is a rigid, electrically conductive trochar whose sharply pointed end extends beyond the end of the tube. The trochar is used to deliver electrical impulses to the tissue at its end. Electrical stimuli can be delivered by means of the trochar 120 by connecting an electrical stimulator (not shown) to connector 122 on the trochar. The initial insertion site of the trochar, guided by a clinical knowledge of tissue landmarks or radiographic images, may be modified until stimulation produces excitation of nerves 8 judged by perceptible sensations or clinical demonstration of desired effects on bladder, periurethral muscle or other pelvic floor musculature. Satisfactory stimulation of nerves 8 will ensure that the end of the rod around the trochar is located in an appropriate site sufficiently close to nerves 8 so that electrical stimulation using the microstimulator will also produce the desired nerve excitation. Insertion of the microstimulator is accomplished by removing trochar 120 and passing the microstimulator through the hollow cannula 110 using, e.g., a blunt-ended push-rod 130.

Figure 3:
FIG. 3 depicts additional exemplary locations for the implantable stimulator.

As mentioned earlier and as depicted in FIG. 3, another preferred stimulation location for purposes of the present invention is on or adjacent the tibial nerve 140. The tibial nerve is relatively easily accessible (i.e., relatively near the overlying skin with no muscle between the nerve and the skin) at two sites in the leg. The first is at the level of the ankle, immediately posterior to the medial malleolus 144, the posterior tibial artery 146, and the posterior tibial vein 148. The second is at the level of the knee, in the popliteal fossa (i.e., the back of the knee), immediately lateral to the popliteal artery 152 and the popliteal vein 154. Other sites along tibial nerve 140, although not as easily accessible, are acceptable stimulator locations.

Figure 4:
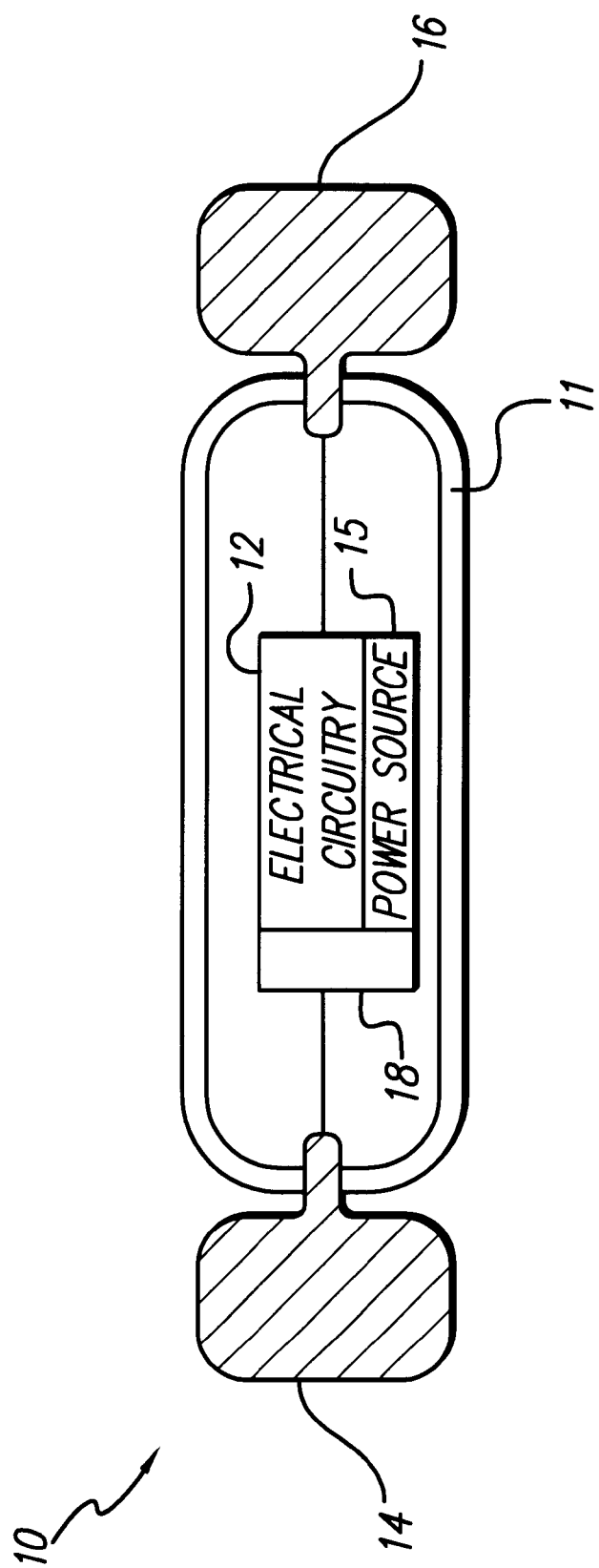
FIG. 4 illustrates an exemplary embodiment of a stimulation system of the present invention.

As depicted in FIG. 4, a preferred device 10 includes a narrow, elongated capsule 11 containing electronic circuitry 12 connected to electrodes 14 and 16, which pass through the walls of the capsule at either end. As detailed in the referenced patents, electrodes 14 and 16 comprise a stimulating electrode (to be placed close to the nerve) and an indifferent electrode (for completing the circuit). Other configurations of device 10 are possible, as is evident from the above-referenced patents.

The implantable stimulator 10 should be sufficiently small to permit its placement near the structures to be stimulated. Capsule 11 preferably has a diameter no greater than about 3–4 mm, and more preferably only about 1.5 mm. Capsule length is preferably no greater than about 20–25 mm, and more preferably only about 10–12 mm. The shape of the microstimulator is preferably determined by the structure of the desired target, the surrounding area, and the method of surgical insertion. A thin, elongated cylinder with electrodes at the ends, as shown in FIG. 4, is currently preferred, but other shapes, such as disks or helical structures, are possible.

The external surfaces of stimulator 10 are advantageously composed of biocompatible materials. Capsule 11 is preferably made of glass or ceramic to provide a hermetic package that will exclude water vapor but permit passage of magnetic fields used to transmit data and power. Electrodes 14 and 16 are preferably made of a noble or refractory metal, such as platinum, iridium, tantalum, titanium, niobium or their alloys, in order to avoid corrosion or electrolysis which could damage the surrounding tissues and the device.

In order to help determine the strength of electrical stimulation required to produce the desired therapeutic effect, in one embodiment, the muscle activity produced in response to stimulation may be detected, e.g., via recording of the associated electromyograph (EMG). Thus, when stimulator 10 is implanted, for example, near the dorsal nerve of the clitoris (a branch of the pudendal nerve), the signals from an EMG sensor built into microstimulator 10 may be used to adjust stimulation parameters. Alternatively, a "microstimulator" dedicated to sensory processes may communicate with a microstimulator that provides the stimulation pulses. For instance, a "microstimulator" may be introduced into the bladder to sense changes in bladder pressure. As described below, the implant circuitry 12 would then amplify and transmit these signals, which may be analog or digital. Other methods of determining the required stimulation include sensing sphincter or colon pressure, sensing muscular activity associated with the sphincter, bladder, or colon via electromyograph, observing the stimulation required to decrease or eliminate pain, and other methods mentioned herein, and others that will be evident to those of skill in the art upon review of the present disclosure.

Figure 5:
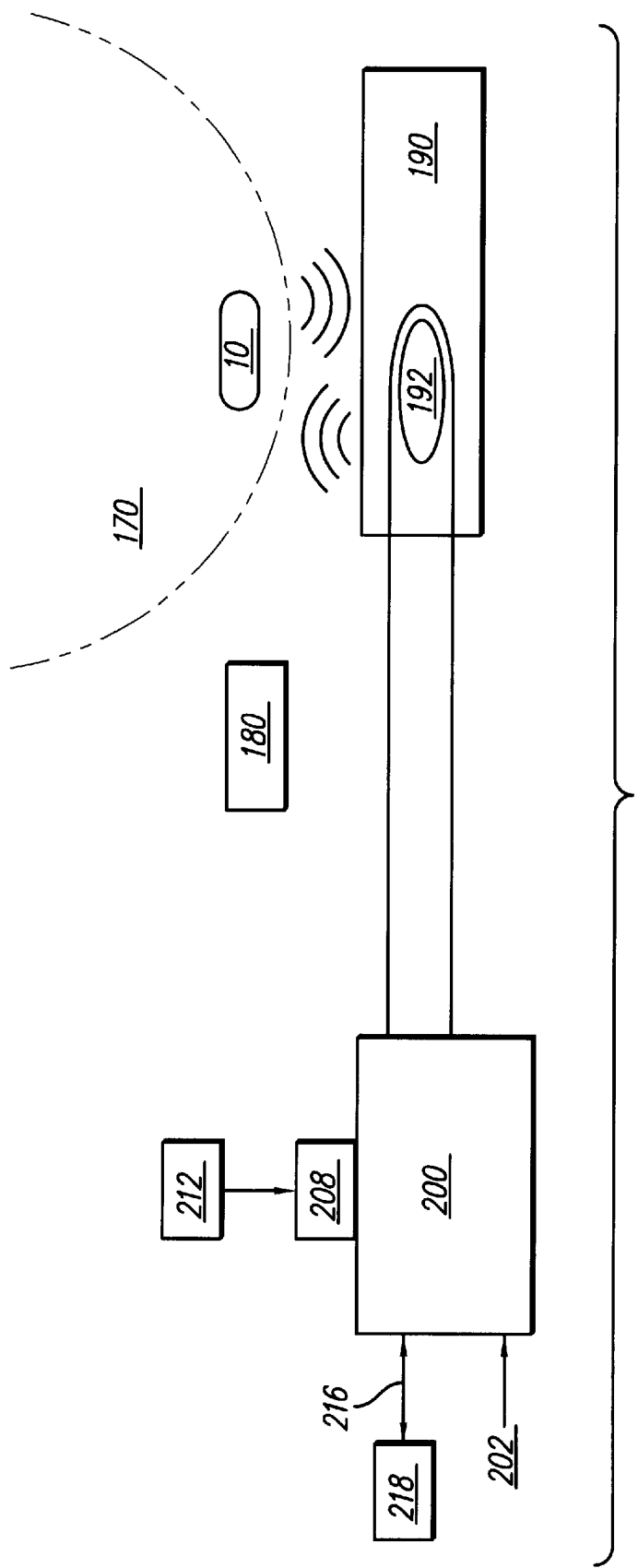
FIG. 5 illustrates external components of the invention.

In another preferred mode of operation, and as illustrated in FIG. 5, the patient 170 may switch the implantable stimulator 10 on and off by use of handheld controller 180. The controller 180 operates to control the implantable stimulator 10 by any of various means, including sensing the proximity of a permanent magnet located in controller 180, or sensing RF transmissions from the handheld controller 180.

The external components related to programming and providing power to implantable stimulator 10 are also illustrated in FIG. 5. When it is required to communicate with implanted stimulator 10, the patient 170 is positioned on or near external appliance 190, which appliance contains one or more inductive coils 192 or other means of communication (e.g., RF transmitter and receiver). External appliance 190 is connected to external electronic circuitry appliance 200 which receives power 202 from a conventional power source. External appliance 200 contains manual input means 208, e.g., a keypad, whereby the patient 170 or a caregiver 212 can request a change in the parameters of the stimulation produced during the normal operation of implantable stimulator 10. In a preferred embodiment, manual input means 208 includes various mechanical switches and visual display devices that provide the patient and/or caregiver with information about the status and prior programming of implantable stimulator 10.

Alternatively or additionally, the external electronic appliance 200 may be provided with an electronic interface means 216 for interacting with other computing means 218, such as by a serial interface cable or infrared link to a personal computer or to a telephone modem. Such interface means 216 would thus permit a clinician to monitor the status of the implant and prescribe new stimulation parameters from a remote location.

The external appliance(s) may advantageously be embedded in a seat cushion, mattress cover, or garment. Other possibilities exist, including a belt, strap, or other structure that may be affixed to the patient's body or clothing.

In a preferred embodiment, one or more external appliances 200 may be provided to accomplish one or more of the following functions:

Function 1: Transmit electrical power from the external electronic appliance 200 via appliance 190 to stimulator 10 in order to recharge the power source/storage device 15. External electronic appliance 200 could further include an automatic algorithm that adjusts stimulation parameters automatically whenever the stimulator(s) 10 is/are recharged.

Function 2: Transmit data from the external appliance 200 via the external appliance 190 to stimulator 10 in order to change the parameters of electrical stimulation produced by the implant electronic circuitry 12.

Function 3: Transmit data regarding pressure, neural activity (e.g., ENG), muscle activity (e.g., EMG), impedance, or other activity recorded in response to electrical stimulation from stimulator 10 to external appliance 200 via external appliance 190.

By way of example, a treatment modality for incontinence may be carried out according to the following sequence of procedures:

1. A first stimulator 10 is implanted so that its electrodes 14 and 16 are located adjacent to nerve fibers 8. A second stimulator 10 is implanted into the bladder.
2. Using Function 2 of external electronic appliance 200 and external appliance 190, the first implantable stimulator 10 is commanded to produce a series of electrical stimulation pulses with gradually increasing amplitude.
3. After each stimulation pulse, Function 3 of the second implantable stimulator 10 is used to record any change in bladder pressure. These responses are converted to data and telemetered out to the external electronic appliance 200 via the external appliance 190.
4. From the response data received at external appliance 200 from the second implantable stimulator 10, the stimulus threshold for obtaining a reflex response is determined and is used by a clinician acting directly 212 or by other computing means 218 to transmit the desired stimulation parameters to the first implantable stimulator 10 in accordance with Function 2.
5. When patient 170 desires to invoke an electrical stimulation to alleviate symptoms, patient 170 employs handheld controller 180 to set the first stimulator 10 in a state where it continuously delivers the prescribed stimulation pattern.
6. Patient 170 employs handheld controller 180 to turn off the first simulator 10, if desired.
7. Periodically, the patient or caregiver recharges the power source/storage device 15 of the first and/or second implantable stimulator 10 in accordance with Function 1.

For the treatment of any of the various types of incontinence, urgency, frequency, or pelvic pain, it may be desirable to modify or adjust the algorithmic functions performed by the implanted and/or external components, as well as the surgical approaches, in ways that would be obvious to skilled practitioners of these arts. For example, it may be desirable to employ more than one implantable stimulator 10, each of which could be separately controlled by means of a digital address. Multiple channels and/or multiple patterns of stimulation might thereby be programmed by the clinician and controlled by the patient in order to deal with complex or multiple dysfunctions such as may occur as a result of spinal cord injury and neurodegenerative disorders.

In one preferred embodiment, microstimulator 10, or a group of two or more microstimulators, is controlled via closed-loop operation. A response to stimulation is sensed via microstimulator 10, or by an additional microstimulator (which may or may not be dedicated to the sensing function), or another implanted or external device. If necessary, the sensed information is transmitted to microstimulator 10. The stimulation parameters used by microstimulator 10 are automatically adjusted based on the sensed information. Thus, the stimulation parameters are adjusted in a closed-loop manner to provide stimulation tailored to the response to stimulation.

For instance, a first and second "microstimulator" are provided. The second "stimulator" periodically (e.g. once per minute) records bladder pressure and transmits it to the first simulator. The first stimulator uses the bladder pressure information to adjust stimulation parameters according to an algorithm programmed, e.g., by a physician. For example, amplitude of stimulation may be increased in response to increased bladder pressure.

While a microstimulator may also incorporate means of sensing incontinence, urgency, frequency, or pain, e.g., via a pressure sensor or electromyograph, it may alternatively or additionally be desirable to use a separate or specialized implantable device to record and telemeter physiological responses in order to adjust stimulation parameters. This information may then be transmitted to an external device, such as external appliance 190, or may be transmitted directly to implanted stimulator(s) 10. However, in some cases, it may not be necessary or desirable to include a sensing function or device, in which case stimulation parameters may be determined and refined, for instance, by patient feedback.

It is thus seen that the invention provides a system which reduces or eliminates the incidence of unintentional episodes of bladder emptying by stimulating nerve pathways that diminish involuntary bladder contractions, improve closure of the bladder outlet, and/or improve the long-term health of the urinary system by increasing bladder capacity and period between emptying. It is also seen that the invention provides a system which similarly reduces or eliminates the incidence of fecal incontinence. It is additionally seen that the invention provides a system that reduces or eliminates pelvic pain by stimulating nerve pathways that derive from the sacral roots, and specifically the tibial nerve.

It is further seen that the invention provides a method whereby a patient can receive one or more patterns of neural stimulation that can be prescribed by a physician and administered without continuous oversight by a clinical practitioner.

Further, it is seen that the invention provides such a system and method using small implantable microstimulators that may be implanted in the desired tissue/nerve-stimulating locations by injection or laparoscopic insertion rather than major surgery.

While the invention herein disclosed has been described by means of specific embodiments and applications thereof, numerous modifications and variations could be made thereto by those skilled in the art without departing from the scope of the invention set forth in the claims.

What is claimed is:

1. A method to remediate incontinence by delivering trains of electrical pulses to nerves (8) supplying tissues in the perineum and pelvic floor (2) through at least one implantable microstimulator (10), each microstimulator (10) comprising a hermetically-sealed chamber separating a plurality of exposed electrodes (14, 16) for delivering electrical current and an electronic means (12) within said chamber for generating electrical current, said microstimulator being of a size and shape capable of implantation through a laparoscope or hypodermic needle; and wherein the at least one microstimulator further includes a self-contained power source housed within the hermetically-sealed chamber for supplying operating power to the electronic means within the at least one microstimulator, and wherein the method further comprises recharging and programming the self-contained power source as needed from an external, non-implanted, location; and further including charging the self-contained power source with sufficient energy to allow the at least one microstimulator to provide a continuous or intermittent simulation throughout the day as needed, wherein the self-contained power source powers the at least one microstimulator to deliver repeated pulses for several hours, thereby providing patients portability that allows them to be free from reliance on radio-frequency power delivery.

2. The method of claim 1 wherein delivery of the electrical pulses to the nerves supplying tissues in the perineum and pelvic floor is supplied through a multiplicity of implantable microstimulators (10).

3. The method of claim 1 further including powering the at least one implantable microstimulator (10) using radio-frequency operating power and control signals received from an external, non-implanted, control unit (20).

4. The method of claim 3 further including using the at least one microstimulator (10) intermittently for only a few hours per day or week to improve the symptomatology of incontinence.

5. A method of treating patients with incontinence, urgency, frequency, and/or pelvic pain, comprising:
   implanting at least one miniature stimulator adjacent to at least one specific nerve or muscle of the patient, wherein the stimulator delivers a stimulus to tissue surrounding the stimulator;
   applying the stimulus to the tissue surrounding the at least one stimulator in order to at least in part alleviate symptoms of the incontinence, urgency, frequency, and/or pelvic pain of the patient being treated,
   wherein the at least one specific nerve or muscle is selected from one or more of the periurethral muscles, urethral sphincter, anal sphincter, pudendal nerve, clitoral or penile branches of the pudendal nerve, inferior rectal branches of the pudendal nerve, urethral branch of the pudendal nerve, pelvic nerve, tibial nerve, pelvic floor nerves, and at least one of the somatic nerves that originate from the sacral nerve roots; and
   wherein the stimulation is delivered at less than about 50 to 100 Hz.

6. The method of treatment of claim 5 wherein the miniature stimulator comprises at least two electrodes, and wherein the stimulus comprises electrical stimulation delivered via the at least two electrodes.

7. A method for treating patients with incontinence, urgency, frequency, and/or pelvic pain, comprising:
   implanting a stimulator having a size and shape suitable for placement adjacent to a nerve that derives from the sacral roots, wherein said implantable stimulator comprises:
     electronic circuitry that generates stimulation pulses in accordance with prescribed simulation parameters;
     at least two electrodes electrically connected to said electronic circuitry through which the stimulation pulses may be delivered to nerves or tissue adjacent to the electrodes;
     a programmable memory for receiving and storing the prescribed stimulation parameters; and
     a power source for providing operating power to said electronic circuitry; and
   providing at least one external appliance for transmitting the prescribed parameters to the implantable stimulator.

8. The method of claim 7 further comprising implanting the implantable stimulator into body tissue through a hypodermic tube or similar sized cannula.

9. The method of claim 7 wherein the at least one implantable stimulator further comprises at least one sensor.

10. The method of claim 9 further comprising sensing a condition using the at least one sensor and adjusting the stimulation parameters based on the sensed condition.

11. The method of claim 10 further comprising performing the parameter adjustment using the at least one external appliance.

12. The method of claim 10 further comprising performing the parameter adjustment using the implantable stimulator.

13. The method of claim 10 further comprising implanting more than one stimulator.

14. The method of claim 13 wherein at least a first stimulator includes at least one sensor and further comprising using the sensed condition to adjust the stimulation parameters of at least a second stimulator.

15. The method of claim 7 further comprising using the power source to store power received from the at least one external appliance.

16. The method of claim 15 wherein the power source is rechargeable.

17. A method for stimulating at least one nerve innervating specific anatomical structures of the perineum, comprising:
   implanting a stimulator having a size and shape suitable for placement adjacent the neuromuscular structures of the pelvic floor, said stimulator having electronic circuitry therein that generates a stimulation pulse in accordance with prescribed stimulation parameters;
   providing at least two electrodes electrically connected to said electronic circuitry through which said stimulation pulse may be delivered to tissue or nerves adjacent the electrodes;
   providing a programmable memory within said stimulator for receiving and retaining said stimulation parameters;
   providing a power source within said implantable stimulator for providing operating power to said electronic circuitry; and
   providing at least one external appliance for transmitting said stimulation parameters to said implantable stimulator.

18. The method of claim 17 wherein said at least one nerve includes the dorsal nerve of the clitoris or the dorsal nerve of the penis, and wherein the method treats urinary urge incontinence and/or detrusor hyperreflexia.

19. The method of claim 17 wherein said at least one nerve innervates the urethra and/or the detrusor muscle, and wherein the method treats urinary retention.

20. The method of claim 17 wherein said at least one nerve innervates the internal and/or external urethral sphincter and/or their intramuscular branches, and wherein the method treats urinary stress incontinence.

21. The method of claim 17 wherein said at least one nerve innervates the clitoris and/or vagina, and wherein the method treats vaginismus, dyspareunia, anorgasmia, and/or other female sexual dysfunctions.

22. The method of claim 17 wherein said at least one nerve innervates the rectum and/or colon, and wherein the method treats constipation, fecal retention and/or colorectal hypomotility.

23. The method of claim 17 further comprising implanting said stimulator into body tissue through a hypodermic tube or similar-sized cannula.

* * * * *